(12) United States Patent
Davig (10) Patent No.: US 8,608,644 B1
(45) Date of Patent: Dec. 17, 2013

(54) REMOTE INTERACTIVE SEXUAL STIMULATION DEVICE

(76) Inventor: Gerhard Davig, Franklin, WI (US)

( * ) Notice: Subject to any disclaimer, the term of this patent is extended or adjusted under 35 U.S.C. 154(b) by 913 days.

(21) Appl. No.: 12/695,927

(22) Filed: Jan. 28, 2010

(51) Int. Cl.
*A61F 5/00* (2006.01)

(52) U.S. Cl.
USPC .............................................. 600/38

(58) Field of Classification Search
USPC .................................. 600/38–41
See application file for complete search history.

(56) References Cited

U.S. PATENT DOCUMENTS

| | | | |
|---|---|---|---|
| 5,853,362 A * | 12/1998 | Jacobs | 600/38 |
| 6,368,268 B1 | 4/2002 | Sandvick et al. | |
| 6,592,516 B2 | 7/2003 | Lee | |
| 6,695,770 B1 * | 2/2004 | Choy et al. | 600/38 |
| 6,786,863 B2 | 9/2004 | Abbasi | |
| 7,046,151 B2 | 5/2006 | Dundon | |
| 7,347,815 B2 | 3/2008 | Serbanescu | |
| 7,395,126 B2 | 7/2008 | Decker | |
| 7,438,681 B2 | 10/2008 | Kobashikawa et al. | |
| 2003/0036678 A1 | 2/2003 | Abbassi | |
| 2005/0138560 A1 * | 6/2005 | Lee et al. | 715/719 |
| 2007/0055096 A1 | 3/2007 | Berry et al. | |

FOREIGN PATENT DOCUMENTS

| | | |
|---|---|---|
| DE | 102004011397 | 11/2005 |
| KR | 20020023282 | 3/2002 |
| KR | 20020093729 | 12/2002 |

* cited by examiner

*Primary Examiner* — John Lacyk
(74) *Attorney, Agent, or Firm* — Michael I. Kroll (57) ABSTRACT

A therapeutic adult cyber sex toy for use over the internet incorporating the premise of video chat interaction with programming capable of supporting interpersonal sexual experience utilizing a set of communicating controllers produced in the form of male and female genitalia. The controllers of the present invention correlate to that of the partner. The male's controller is in the form of a mock vagina having an optical sensor at its opposed end along with buttons for inducing commands in a linked female's controller, the female controller is in the form of a dildo and has a similar command interface for interacting with the male's controller. Partners are capable of affecting each others experience by varying settings in the others controller while using their own, such variables can include vibration, heat, auditory/video feedback and frequency.

8 Claims, 9 Drawing Sheets

REMOTE INTERACTIVE SEXUAL STIMULATION DEVICE

BACKGROUND OF THE INVENTION

1. Field of the Invention

The present invention relates generally to sex therapy devices and, more specifically, to a therapeutic adult cyber sex toy for use over the internet incorporating the premise of video chat interaction with programming capable of supporting interpersonal sexual experience utilizing a set of communicating controllers produced in the form of male and female genitallia. The controllers of the present invention correlate to that of the partner. The male's controller is in the form of a mock vagina having an optical sensor at its opposed end along with buttons for inducing commands in a linked female's controller, the female controller is in the form of a dildo and has a similar command interface for interacting with the male's controller. Partners are capable of affecting each others experience by varying settings in the others controller while using their own, such variables can include vibration, heat, auditory/video feedback and frequency.

2. Description of the Prior Art

There are other computerized sex toy devices designed for sex play. While these cyber sex toys may be suitable for the purposes for which they were designed, they would not be as suitable for the purposes of the present invention, as hereinafter described.

SUMMARY OF THE PRESENT INVENTION

A primary object of the present invention is to provide an online computer interface for cyber sex wherein cyber sex partners can link and share the use of specially formed controllers having the form of a mock vagina for male users and a dildo for female users.

Still another object of the present invention is to provide an online computer interface for cyber sex that enables couples to have sexual relations without the risk of spreading STD's and unwanted pregnancies.

Yet another object of the present invention is to provide an online computer interface for cyber sex to strengthen long distance relationships such as those between serviceman and women and their spouses by enabling them to maintain sexual relations therewith.

Another object of the present invention is to provide an online interface for cyber sex having controllers with variable heat, vibration, frequency, audio/visual and contextual communication Yet another object of the present invention is to provide online interface for cyber sex having controllers with a set of controls that work in communication with the internet to control the user's partner's device settings.

Still yet another object of the present invention is to provide online interface for cyber sex having an on line sensor in its distal end in order to determine movement angles and displacement of the controller.

Another object of the present invention is to provide online interface for cyber sex whereby a physical sexual session can take place without actual physical contact.

Additional objects of the present invention will appear as the description proceeds.

The present invention overcomes the shortcomings of the prior art by providing a therapeutic means for partners to conduct a cyber sex session utilizing video, audio and contextual interface having controllers adapted to simulate male and female genitalia thereby eliminating the spread of STD's and unwanted pregnancy. Additionally said controllers have a set of controls for varying and setting the functions of their partners controller during interface.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Turning now descriptively to the drawings, in which similar reference characters denote similar elements throughout the several views, the figures illustrate the Therapeutic Interactive Online Sexual Stimulation Device of the present invention. With regard to the reference numerals used, the following numbering is used throughout the various drawing figures.

10 Therapeutic Interactive Online Sexual Stimulation Device of the present invention
11 controller panel
12 female
16 female controller
18 male
20 male controller
24 male interface monitor
26 female interface monitor
27 mock penis "A"
28 mock Penis "B"
30 mock penis "C"
32 double hinge
34 housing
36 cable
38 cable port
40 start button
42 heat control button
44 vibration control button
46 online interface/modem
48 universal TV remote 50 user persona
52 battery
54 vibration unit
56 thermally conductive soft material
58 heater element
60 mock penis
62 mock vagina
64 inlet
66 biography screen
68 web cam
70 optical receiver
72 chat screen
74 orifice
76 signal
78 video screen
80 control status bar
82 caricature
84 caricature characteristics

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Figure 1:
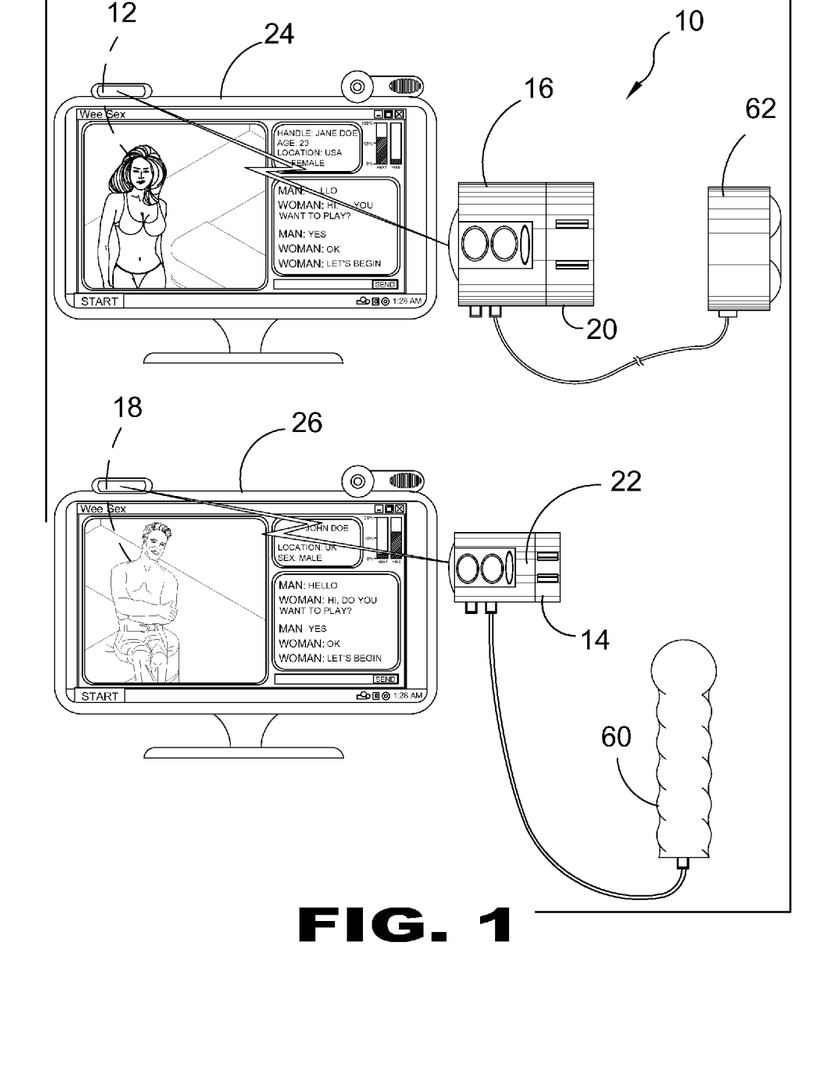
FIG. 1 is an illustrative view of the present invention in use.

Referring to FIG. 1, shown is an illustrative view of the present invention in use. Shown is the therapeutic remote interactive sexual device 10 utilizing a set of pre programmable controllers formed to simulate either male or female genitalia. In typical hetero game play the female 12 utilizes the male's controller 22 to operate a mock vagina 62, while the male 18 utilizes the female controller 16 to operate a simulated penis 60. The online 46 interfaces of the two units transmit a signal 76 to the optical receivers 70 of a male interface monitor 24 and a female interface monitor 26 to allow the users to view the action. The objective of the present invention is to enable couples to have sexual relations without the risk of spreading STD's or unwanted pregnancies. It can also be used as treatment for erectile dysfunction.

Figure 2:
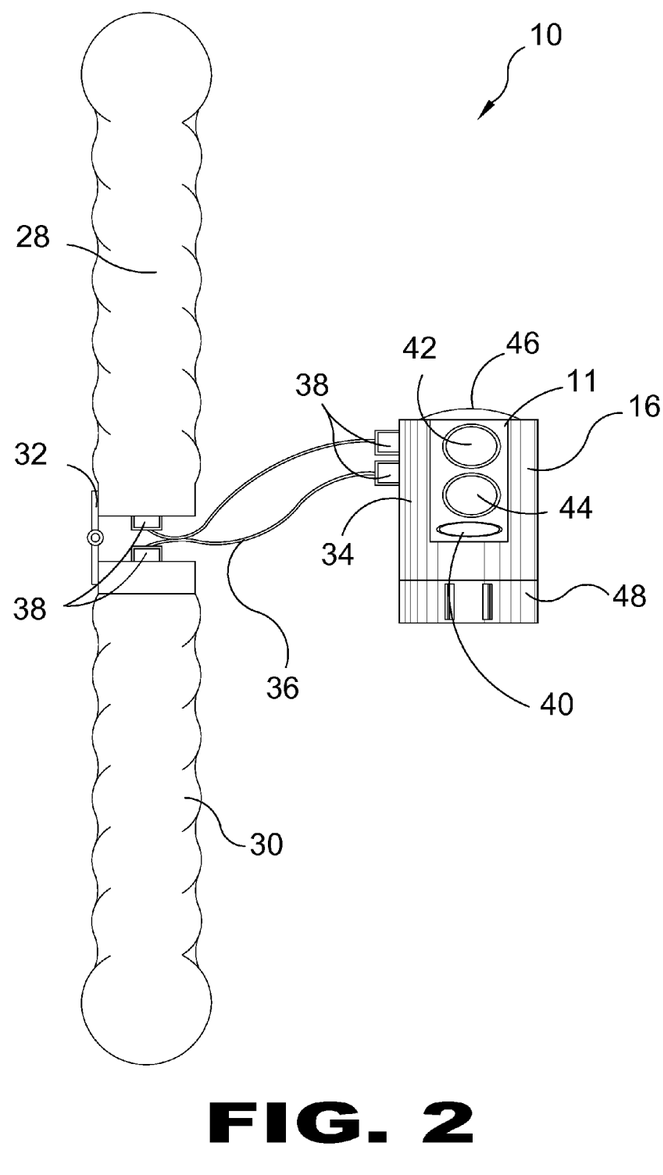
FIG. 2 is a side view of the present invention.
Figure 3:
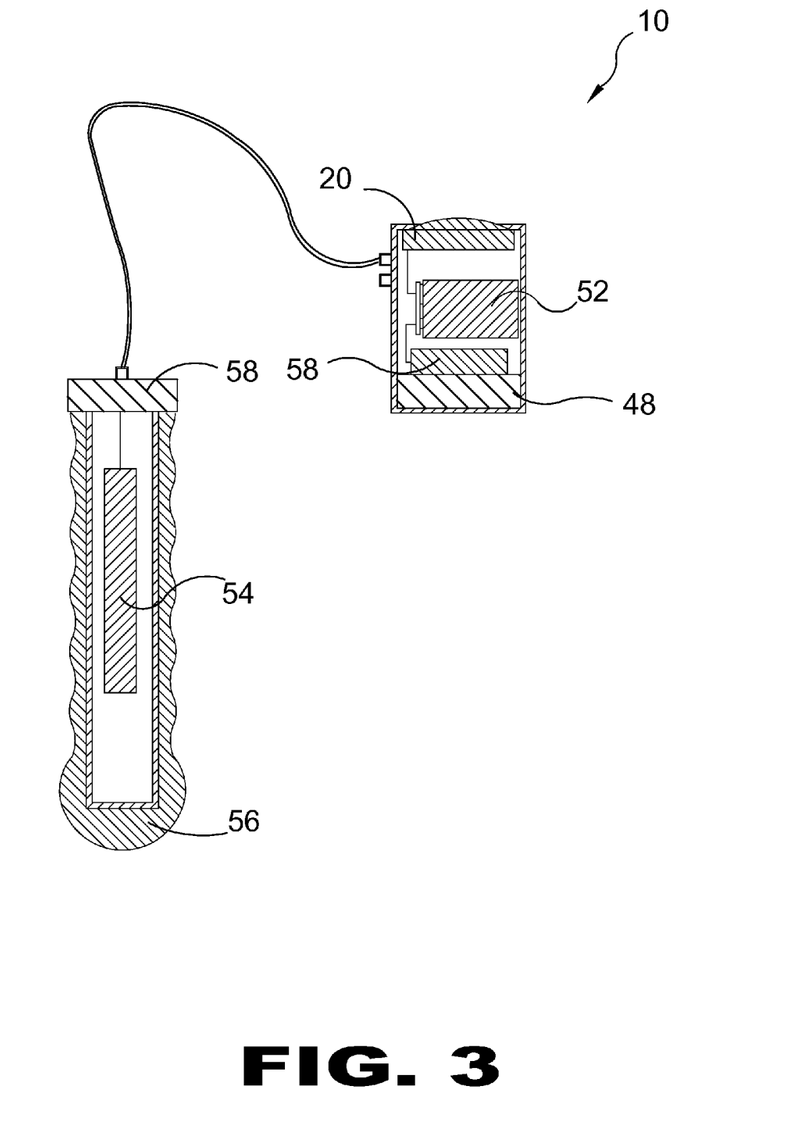
FIG. 3 is a sectional view of the present invention.

Referring to FIG. 2, shown is a side view of the present invention. Shown is the therapeutic remote interactive sexual device 10 with the female controller 16 arranged with a plurality of mock penises for double and triple penetration. The female controller 16 comprises a mock penis "B" 28 hinged 32 to mock penis "C" 30. Mock penis "A" 27 has a housing 34 with a universal remote 48, an online interface/modem 46 and a controller panel 11 comprising a start button 40, a heat control button 42 and a vibration control button 44. A pair of cable ports 38 have a cable 36 connecting the housing 34 to their respective ports 38 on the other mock penises to provide power and commands thereto.

Referring to FIG. 1, shown is a sectional view of the present invention. Shown is the female controller 16 that sends commands to the male controller. Also shown are the heater elements 58, and on line interface/modem 46. Encased in a soft material casing 50 with a battery 52 to power vibrational elements 54, universal remote 48 and online interface 20 for acting upon the mock penis. Additionally shown is the thermally conductive material 56 for transferring heat from the heater element 58 to the interior of the mock vagina 62. The online interface/modem 20 serves to send commands to the male controller.

Figure 4:
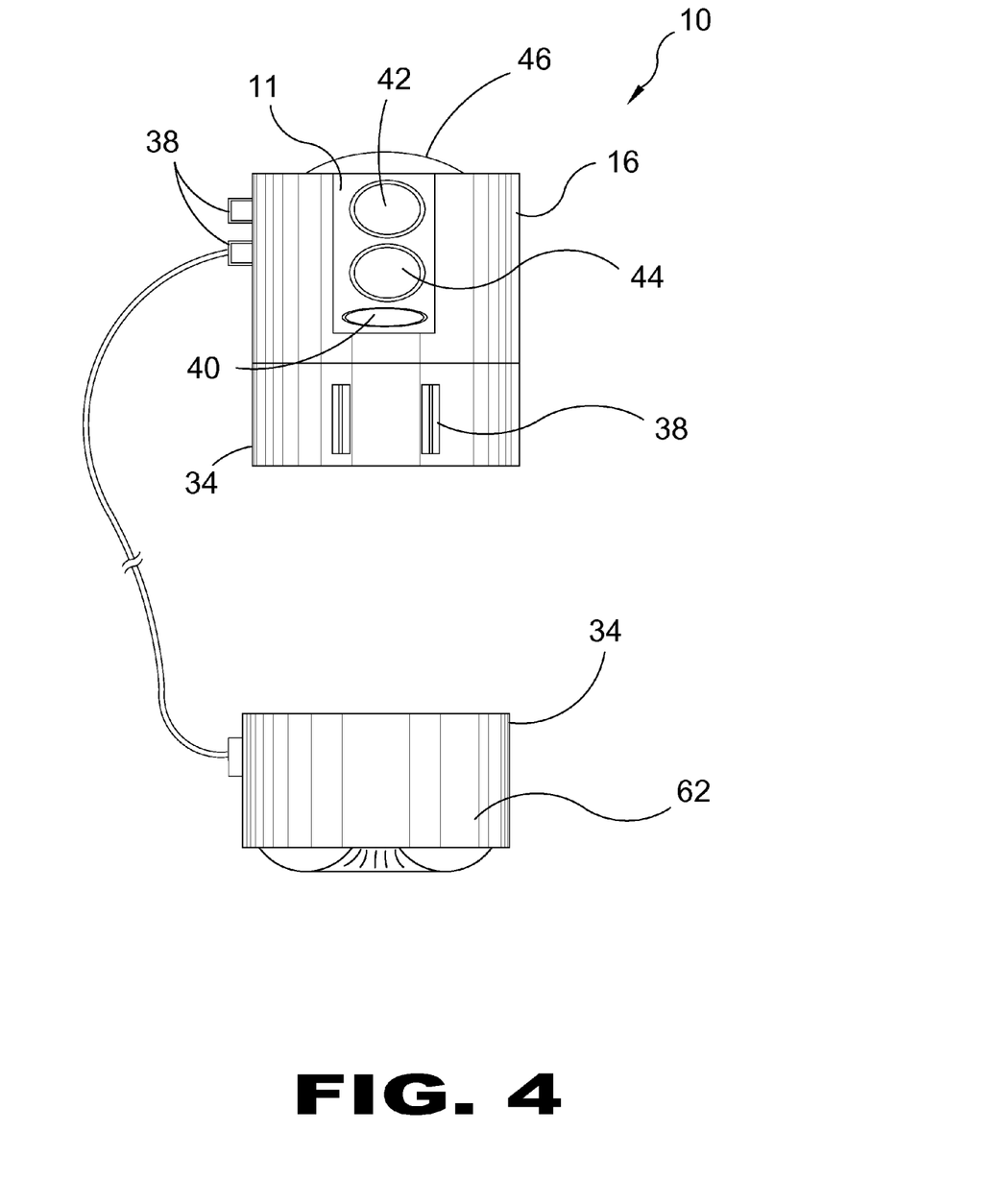
FIG. 4 is a side view of the present invention.

Referring to FIG. 4, shown is a side view of the present invention. Shown is the female controller 16 having a mock vagina 60. Shown is a housing 34 having a pair of cable ports 38 having a control panel 11 with a start button 40, a vibration control button 44, a heat control button 42 and an online interface/modem 46 for controlling a partner's controller's actions.

Figure 5:
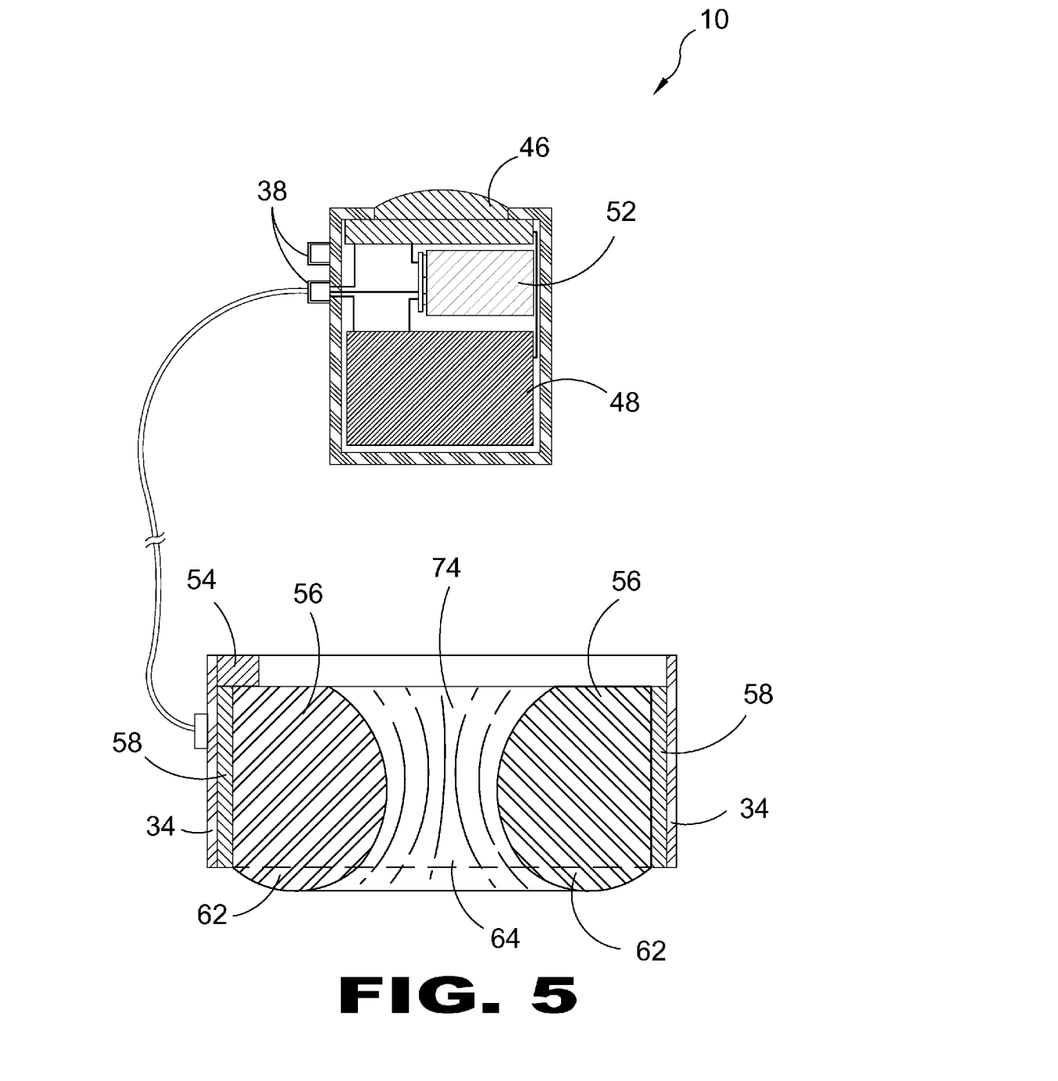
FIG. 5 is a sectional view of the present invention.

Referring to FIG. 5, shown is a sectional view of the present invention. Shown is the female controller 16 with a mock vagina 62 with a housing 34 with heater elements 58 and thermally conductive material 56 surrounding a soft material 50 forming an orifice 74 defining the mock vagina 62. Also shown are the universal remote 48, inlet 62, vibration unit 54 and battery 52.

Figure 6:
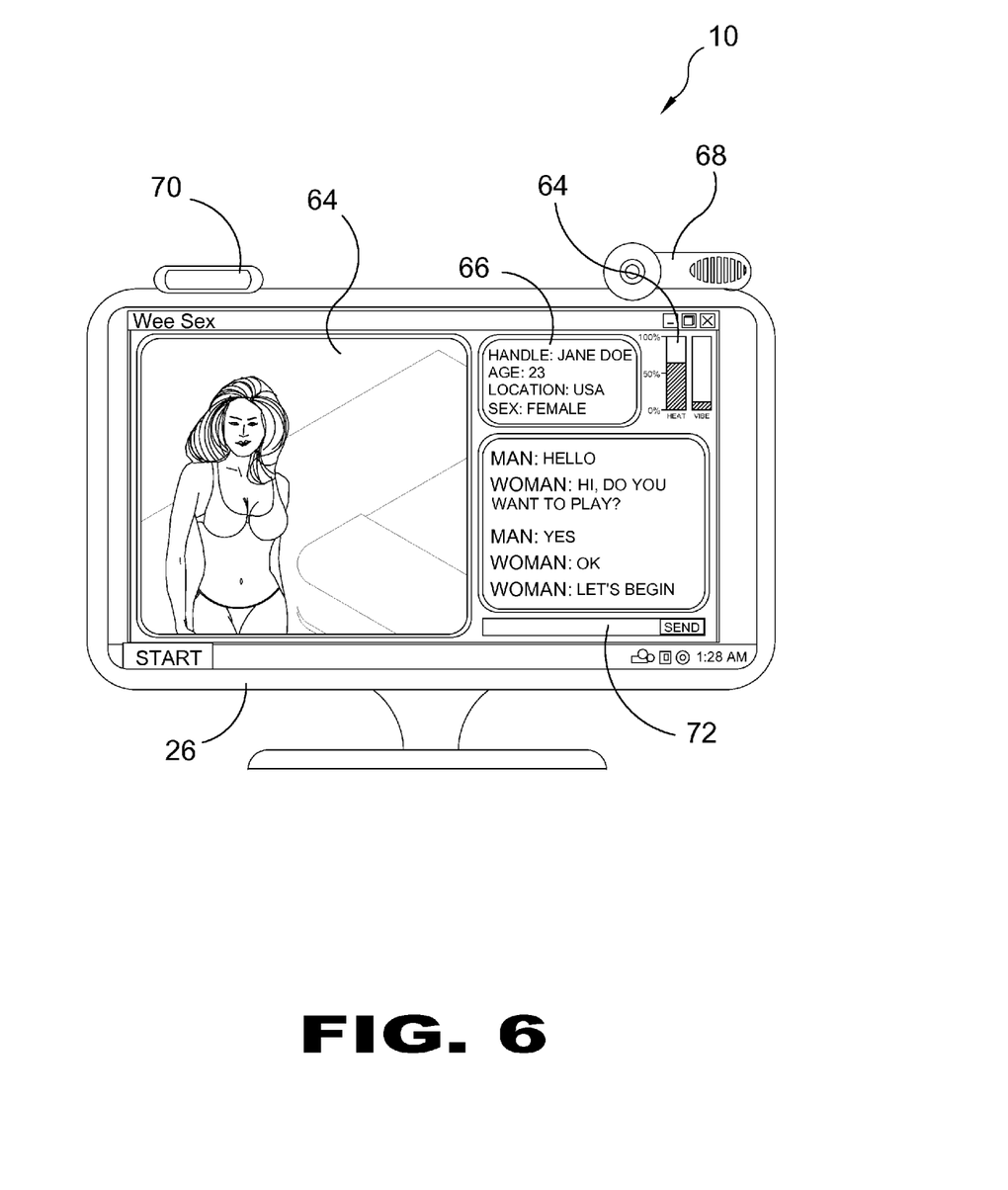
FIG. 6 is a front view of the present invention.

Referring to FIG. 6, shown is a front view of the interface monitor 24 of the present invention 10 having screens for a video feed 78, bio 66 and chat 72. Further included is an optical receiver 70, web cam 68 and controller status bar 80.

Figure 7:
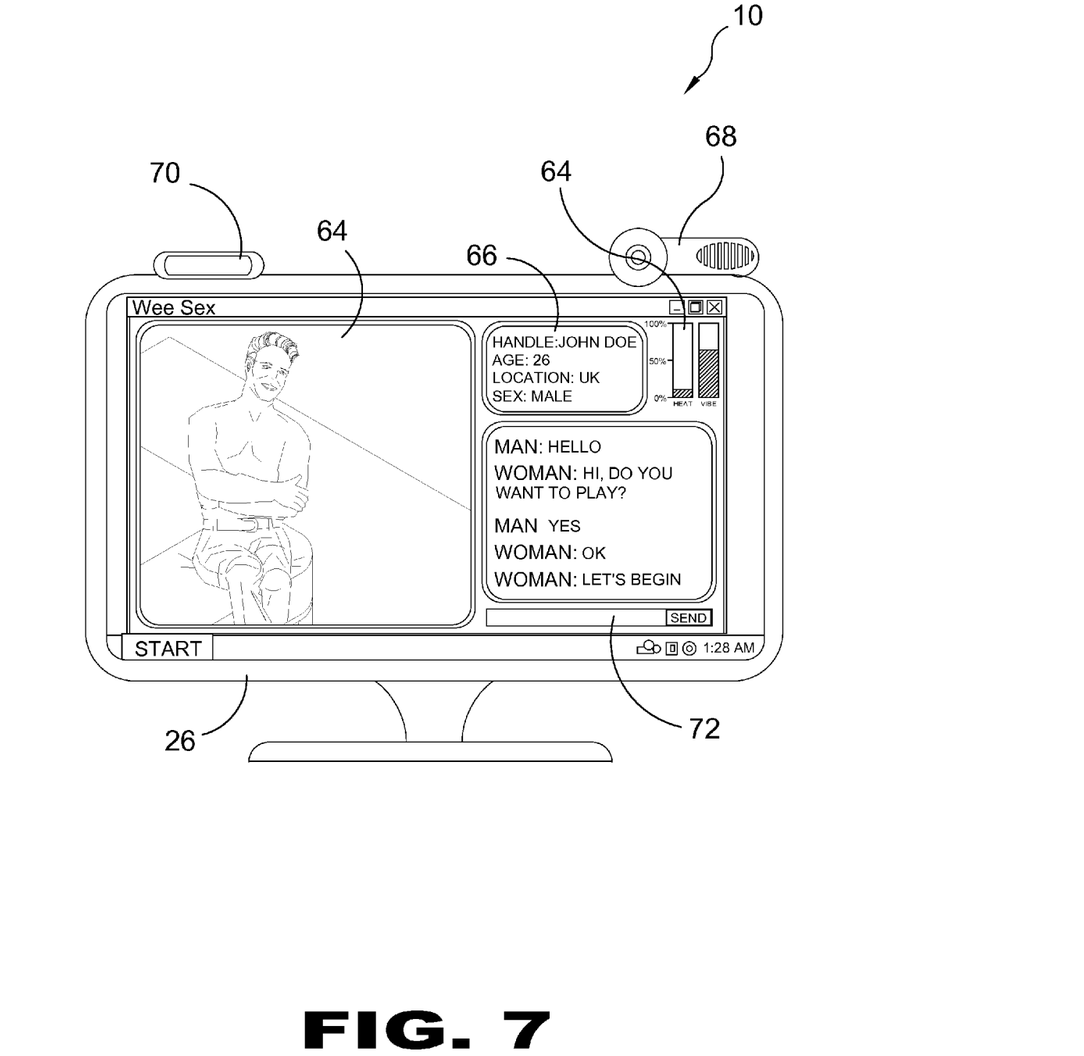
FIG. 7 is a front view of the present invention in use.

Referring to FIG. 7, shown is a front view of the interface monitor 26 of the present invention 10 having screens for a video feed 78, bio 66 and chat 72. Further included is an optical receiver 70, web cam 68 and controller status bar 80.

Figure 8:
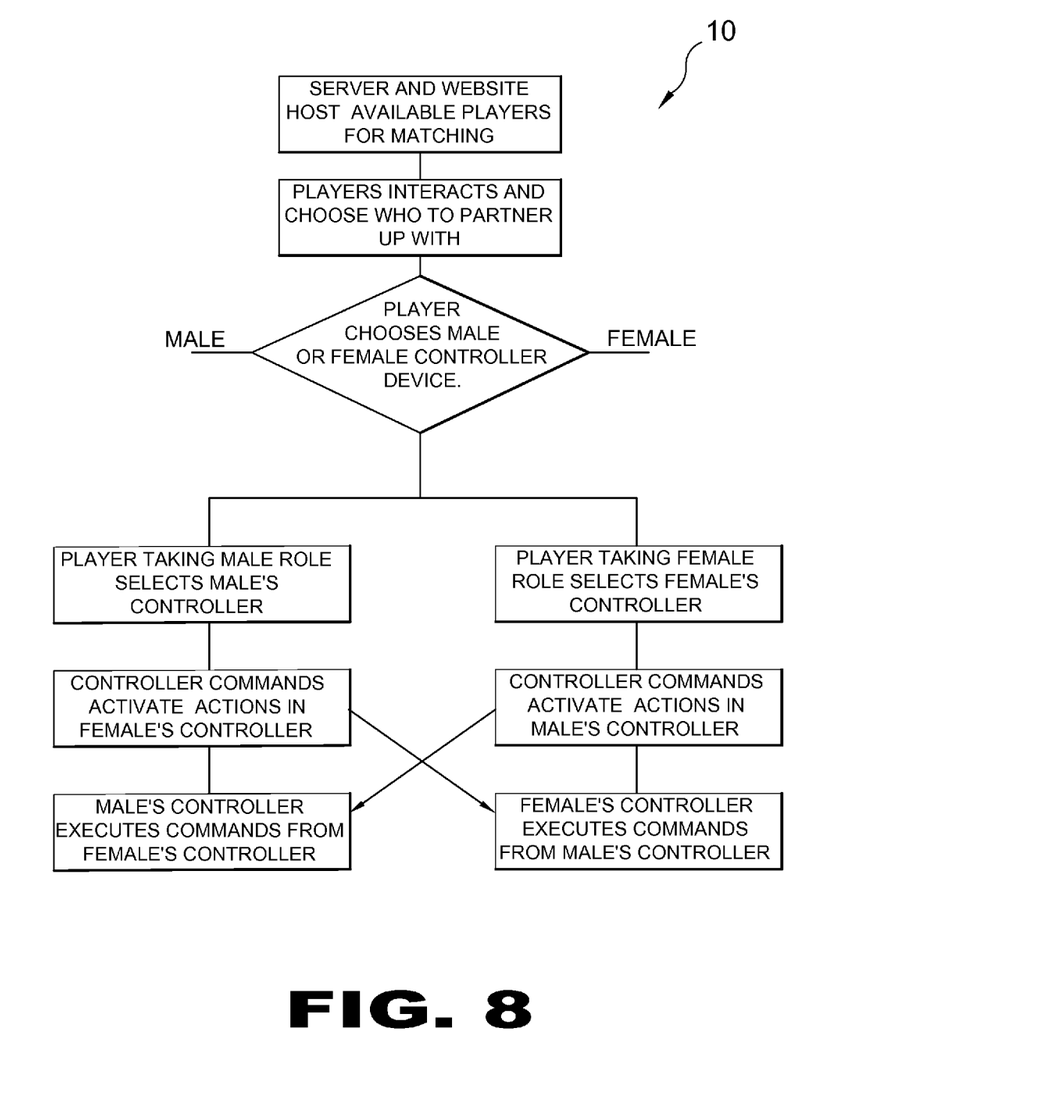
FIG. 8 is a flow chart of the present invention.

Referring to FIG. 8, shown is a flow chart of the present invention 10. Shown is a flow chart of the present invention 10 depicting the flow of actions taken by a pair of users while in use.

Figure 9:
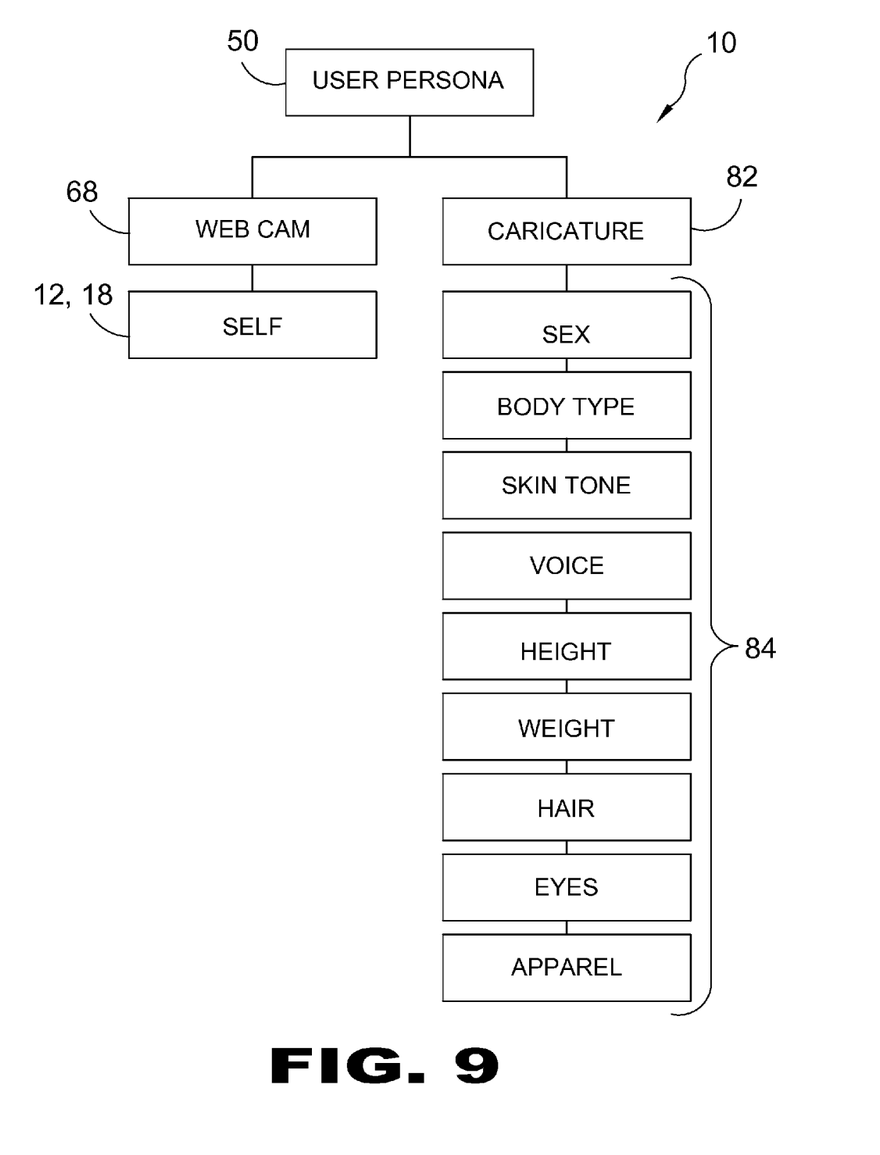
FIG. 9 is a chart of a user's selectable displayable image provided by the present invention.

Referring to FIG. 9, shown is a chart of a user's selectable displayable image provided by the present invention. Users of the present invention 10 are provided with a choice of online persona 50, which is whether to display themselves 12, 18 through web cam 68 or to assume a crafted caricature 82 that will be used during an interactive session. The advantages range from privacy concerns to role playing by creating a caricature 84 where an individual can role play as someone other than themselves. This can range from assuming an online appearance of definable physical characteristics 84, of sex, body type, skin tone, voice, height, weight, hair, eyes and apparel. The present invention provides that a user may desire to appear using any combination of the above features 84 or any single characteristic through the present invention's software editing of a scene prior to transmission. In such a scenario, any physical trait 84 can be modified, including hair color, eye color, body part augmentation or reduction. Thereby enabling users who wish to appear as themselves some level of anonymity through subtle changes. Furthermore, the present invention envisions that the audio portion may include assuming a cultural voice over.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A therapeutic remote interactive sex device comprising:
   a) a female interface monitor incorporating a video display of a male and communicating with said male;
   b) a male controller for enabling the female to control the operation of a remote mock vagina;
   c) a male interface monitor incorporating a video display of a female and communicating with said female;
   d) a female controller for enabling the male to control the operation of a first remote mock penis;
   e) whereby said male is able to insert his penis into said mock vagina and said female is able to insert said first mock penis into her vagina;
   f) said mock vagina comprising an orifice formed by a thermally conductive material, heating elements, and a vibration unit;
   g) said first mock penis comprising an outer layer of thermally conductive material and containing a vibrator;
   h) a second mock penis connected using a hinge to said first mock penis for allowing double penetration, each mock penis being independently controlled, said hinge having a pair of arms extending outwardly and each arm attached to one side of each mock penis adjacent a base of each mock penis, so that in a standby position each of said mock penis' are aligned and pointed away from each other, each base of each mock penis having a cable port; and
   i) whereby said interface monitors allow said male and female to view actions taking place.

2. A therapeutic remote interactive sex device according to claim 1, wherein said male controller further includes a control panel comprising a start button, a heat control button and a vibration control button for enabling the male to control operation of the functions of each mock penis.

3. A therapeutic remote interactive sex device according to claim 2, wherein said female controller further includes a control panel comprising a start button, a heat control button and a vibration control button for enabling the female to control operation the functions of said mock vagina.

4. A therapeutic remote interactive sex device according to claim 3, wherein each of said controllers includes a universal remote.

5. A therapeutic remote interactive sex device according to claim 4, wherein said female controller further includes a battery, an inlet, a universal remote and an on line interface/modem.

6. A therapeutic remote interactive sex device according to claim 3, wherein said male controller and said female controller include online interface units to communicate with one another.

7. A therapeutic remote interactive sex device according to claim 6, further including male interface monitor and female interface monitors communicating with said online interface/modem units.

8. A therapeutic remote interactive sex device according to claim 7, wherein said interface monitors comprise:
   a) a video screen feed,
   b a user biography screen:
   c) a chat screen:
   d) a control status bar; and
   e) a web cam.

* * * * *